United States Patent [19]

Saito

[11] Patent Number: 5,107,006
[45] Date of Patent: Apr. 21, 1992

[54] CLATHRATE COMPOUNDS OF NUCLEAR-SUBSTITUTED SALICYCLIC ACID SALTS

[75] Inventor: Toranosuke Saito, Osaka, Japan

[73] Assignee: Sanko Kaihatsu Kagaku Kenkyusho, Ibaraki, Japan

[21] Appl. No.: 613,733

[22] PCT Filed: Apr. 6, 1990

[86] PCT No.: PCT/JP90/00467
§ 371 Date: Dec. 5, 1990
§ 102(e) Date: Dec. 5, 1990

[87] PCT Pub. No.: WO90/11994
PCT Pub. Date: Oct. 18, 1990

[30] Foreign Application Priority Data

Apr. 7, 1989 [JP] Japan .................................. 1-87056

[51] Int. Cl.$^5$ .............................................. C07F 3/06
[52] U.S. Cl. ..................................... 556/132; 556/149; 556/150
[58] Field of Search ......................... 556/132, 149, 150

[56] References Cited

U.S. PATENT DOCUMENTS 3,983,292  9/1976  Saito et al. ............................ 428/306
4,914,219  4/1990  Satomura et al. .................... 556/132

FOREIGN PATENT DOCUMENTS 0322091  6/1989  European Pat. Off. .
0370389  5/1990  European Pat. Off. .
1190650  7/1989  Japan .................................... 556/132
2017090  10/1979  United Kingdom ................. 556/132

*Primary Examiner*—José G. Dees
*Assistant Examiner*—Porfirio Nazario
*Attorney, Agent, or Firm*—Kane, Dalsimer, Sullivan, Kurucz, Levy, Eisele & Richard

[57] ABSTRACT

The clathrate compound according to the present invention which comprises, as host crystals, crystals of a polyvalent metal salt of a specific nuclear-substituted salicylic acid or a hydrate thereof and, as a gest molecule, an organic compound having 1 to 12 carbon atoms is well soluble in organic solvents or organic compounds having relatively low polarity and has good stability to light rays and $NO_x$ gases and, therefore, the clathrate compound has excellent properties favorable for use as antibiotics, stabilizers for polymeric compounds and developers for recording materials.

7 Claims, No Drawings

CLATHRATE COMPOUNDS OF NUCLEAR-SUBSTITUTED SALICYCLIC ACID SALTS

TECHNICAL FIELD

The present invention relates to a clathrate compound of a nuclear-substituted salicylic acid salt. The clathrate compound of a nuclear-substituted salicylic acid salt, whose gest molecule is an organic compound, according to the present invention is easily soluble in organic solvents or organic compounds having relatively low polarity and has high stability to light rays and $NO_x$ gases and, therefore, the clathrate compound is suitable for use as an antibiotic, a stabilizer for polymeric compounds or a developer for recording materials.

BACKGROUND ART

Nuclear-substituted salicylic acid and salts thereof have high antibiotic action and have been used as antibiotics (see Japanese Patent Unexamined Publication (hereinafter referred to as "J. P. KOKAI") No. Sho 62-153245). Polyvalent metal salts of a nuclear-substituted salicylic acid have been used as stabilizers for halogen atom-containing polymeric compounds such as polyvinyl chloride (see J. P. KOKAI No. Sho 56-112955). In addition, a polyvalent metal salt of a nuclear-substituted salicylic acid, in particular zinc salt thereof has been used as a developer for recording materials (see J. P. KOKAI Nos. Sho 48-98914, Sho 62-25086 and Sho 63-186729). Moreover, J. P. KOKAI No. 63-293464 which was previously filed by the instant applicant discloses that specific nuclear-substituted salicylic acids and salts thereof are suitable for use as antibiotics, stabilizers for polymeric compounds or developers for recording materials.

DISCLOSURE OF THE INVENTION

The object of the present invention is to improve specific polyvalent metal salts of nuclear-substituted salicylic acids or hydrates thereof in stability to light rays and $NO_x$ gases by converting them into clathrate compounds whose gest molecule is an organic compound and to thus make these compounds more favorable for use as antibiotics, stabilizers for polymeric compounds and developers for recording materials.

According to the present invention, there is provided a clathrate compound of a nuclear-substituted salicylic acid salt which comprises, as a host, crystals of a polyvalent metal salt of a nuclear substituted salicylic acid represented by the following general formula (I) or a hydrate thereof and, as a gest molecule, an organic compound having 1 to 12 carbon atoms:

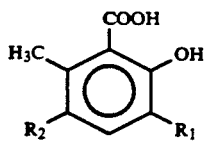

(I)

(wherein $R_1$ and $R_2$ each represents a tert-butyl group, a tert-amyl group, a tert-octyl group or an $\alpha,\alpha$-dimethylbenzyl group). The compound is easily soluble in organic solvents or organic compounds having relatively low polarity and improved in stability to light rays and $NO_x$ gases. Therefore, the compound has enhanced practical value as an antibiotic, a stabilizer for polymeric compounds or a developer for recording materials.

The clathrate compounds are also called inclusion compounds and are crystalline substances which comprise a host crystal constituting the skeletal structure of the crystal and a gest molecule occupying spatial interstices of the host crystal. Therefore, any clathrate compound cannot be formed if there are not present sufficient spatial interstices in the skeletal structure of a crystal. The nuclear-substituted salicylic acid salts rarely form clathrate compounds and the formation of clathrate compounds is a characteristic property peculiar to the polyvalent metal salts of the specific nuclear-substituted salicylic acid represented by the foregoing general formula (I). For instance, a small amount of water is simply coordinated to the polyvalent metal atom in a polyvalent metal salt of 3-($\alpha,\alpha$-dimethylbenzyl)-6-methylsalicylic acid, 3,5-di-tert-butylsalicylic acid, 3,5 di-tert-amylsalicylic acid or 3,5-di-($\alpha,\alpha$-dimethylbenzyl)salicylic acid which has a molecular structure similar to that for the compound of Formula (I) and there is no evidence for the formation of any clathrate compound of the foregoing similar compounds. On the other hand, zinc 3,5-di-($\alpha,\alpha$-dimethylbenzyl)-6-methylsalicylate is obtained in the form of a crystal having up to 3 water molecules per zinc atom and it is found that two water molecules are released under drying conditions of a temperature of about 50° C. and a humidity of about 30% and that if the dried crystals are allowed to stand in a room maintained at a temperature of about 20° C. and a humidity of about 80%, the crystals again recover two water molecules per metal atom. Since there is not observed any change in the crystalline structure of the compound before and after these two processes, the zinc salt having 3 water molecules per zinc atom is no more than a clathrate compound which comprises, as the host crystal, zinc 3,5-di-($\alpha,\alpha$-dimethylbenzyl)-6-methylsalicylate . monohydrate crystals and two water molecules per zinc atom as the gest molecule. Further, the spatial interstices in the skeletal structure of the host crystal is considered to be greater than that required for being occupied by two water molecules while the mobility of these two water molecules is taken into consideration. In fact, it was found that the spatial interstices can be occupied by a variety of organic compounds greater than water molecule.

BEST MODE FOR CARRYING OUT THE INVENTION

The nuclear-substituted salicylic acid salts capable of forming the host crystals are polyvalent metal salts of the nuclear-substituted salicylic acids represented by the foregoing general formula (I) or hydrates thereof and specific examples thereof include polyvalent metal salts of nuclear-substituted salicylic acid such as 3,5 di-tert-butyl-6-methylsalicylic acid, 3 tert butyl-5-($\alpha,\alpha$-dimethylbenzyl)-6-methylsalicylic acid, 3,5-di-tert-amyl-6-methylsalicylic acid, 3-tert-octyl-5-tert-butyl-6-methylsalicylic acid, 3-tert-octyl-5-($\alpha,\alpha$-dimethylbenzyl)-6-methylsalicylic acid, 3 ($\alpha,\alpha$-dimethylbenzyl)-5-tert-butyl-6-methylsalicylic acid and 3,5-di-($\alpha,\alpha$-dimethylbenzyl)-6-methylsalicylic acid, or hydrates thereof. The polyvalent metal salts may exist in the form of neutral salts in which the nuclear-substituted salicylic acid serves as a monobasic acid or in the form of basic salts in which the nuclear-substituted salicylic acid serves as a dibasic acid. Preferred examples of polyvalent metals which form the polyvalent metal salts of the nuclear-substituted salicylic acid are magnesium, aluminum, calcium, iron, cobalt, nickel, zinc and strontium and most preferred is calcium or zinc.

The gest molecules preferably have a size suitable for occupying the crystalline interstices in the skeletal structure of the host crystals. If the size of the gest molecules is too small, the molecules are easily released from the interstices and the resulting clathrate compounds have insufficient stability. On the other hand, if it is too great, the molecules cannot enter into the interstices of the crystals. In the present invention, the gest molecules are organic compounds having 1 to 12 carbon atoms and specific examples thereof are formic acid, methanesulfonic acid, ethylene glycol, acetic acid, acetamide, propanol, isopropanol, 1,3-propanediol, propionic acid, acrylic acid, acrylamide, butanol, isobutanol, tert-butanol, 1,4-butanediol, diethylene glycol, $\beta$-thiodiglycol, butyric acid, methacrylic acids, succinic acid, succinimide, pentanol, 1,5-pentanediol, 1,6-hexanediol, triethylene glycol, cyclohexanol, caproic acid, adipic acid, thiodipropionic acid, 1,8-octanediol, tetraethylene glycol, 4,4'-dihydroxybutyl ether, caprylic acid, 1,10-decanediol, sebacic acid, 1,12-dodecanediol or lauric acid. The behavior of these gest molecules having a molecular weight of not more than about 80 differs from that of those having a molecular weight of more than 80. For instance, neutral zinc 3,5-di-($\alpha,\alpha$-dimethylbenzyl) -6-methylsalicylate . monohydrate can include two molecules of a gest organic compound having a low molecular weight, while the zinc salt can include only one molecule of a gest organic compound having a high molecular weight.

The methods for preparing the clathrate compounds of the nuclear-substituted salicylic acid salt according to the present invention vary depending on the kinds of the nuclear-substituted salicylic acid salts and the gest molecules. If the gest molecule is soluble in water, in many cases, the clathrate compounds may directly obtained by a double decomposition method which comprises previously adding the gest molecule to an aqueous solution of an alkali metal nuclear-substituted salicylate and then gradually adding an aqueous solution of a polyvalent metal salt to the resulting mixture to separate out the corresponding polyvalent metal salt of the nuclear-substituted salicylic acid. At this stage, the clathrate compound is smoothly prepared if each aqueous solution is appropriately heated. Alternatively, the clathrate compound may preferably be prepared according to a gest molecule exchanging method which comprises mixing desired gest molecules with a clathrate compound comprising a polyvalent metal salt of a nuclear-substituted salicylic acid and water molecules or easily releasable gest molecules such as methanol or ethanol molecules with heating, melting or dissolving the entire mixture and then cooling the mixture to crystallize the resulting clathrate compound. In this gest molecule-exchange reaction, the operations can smoothly be performed if an inert organic solvent which does not serve as a gest molecule is added to the reaction system and the presence of a small amount of water is desirable. The gest molecule-exchange method may also be performed in a heterogeneous system in which water is a medium. During the exchange reaction, the exchange velocity can be improved by sufficiently heating the system and the dispersing properties of the system is improved by the presence of a small amount of a surfactant.

The present invention will hereunder be explained in more detail with reference to the following specific Examples, Comparative Examples and Reference Examples.

EXAMPLE 1

To a four-necked 2,000 ml volume flask of hard glass provided with a stirring machine, a thermometer, a dropping funnel and a reflux condenser, there were added 700 g of water, 300 g of isopropanol and 150 g of sodium 3,5-di-tert-butyl-6-methylsalicylate and the flask was heated with stirring to thus control the temperature of the contents of the flask to 50° C. After dissolution of the sodium salt, 220 g of a 20% aqueous solution of zinc sulfate was dropwise added to the flask through the dropping funnel over about 3 hours. The contents of the flask was maintained at a temperature of 50° C. during the dropwise addition. Subsequently, the products of this double decomposition was ripened for about one hour, cooled to 30 and then filtered under suction. The resultant filter cake was washed with about 500 ml of water and was dried at 50° C. and 30 Torr to thus give 190 g of white crystalline powder. The water content of the product was determined according to Karl Fischer method and found to be 2.62% (estimated theoretical value: 2.47%). Alternatively, the product was analyzed by gas chromatography method due to thermal decomposition in which toluene was used as an internal standard and acetone was used as a solvent and it was found that the product contained 15.9% of isopropanol (estimated theoretical value: 16.46%). The product was further analyzed by chelatometric titration and it was confirmed that the product contained 9.00% (estimated theoretical value: 8.95%) of zinc. These results demonstrate the justifiability of the assumption that the product was a clathrate compound which comprises, as the host crystal, neutral zinc 3,5-di-tert-butyl-6-methylsalicylate . monohydrate and two isopropanol molecules as the gest molecule. According to the NMR spectroscopic analysis of the product, it could not be distinguished from the mixture having the estimated ratio of the host crystal component to the gest molecular component. When the product was subjected to thermal analysis at ordinary pressure, it was observed that a water molecule was released subsequently to the releasing of two isopropanol molecules at a temperature of 120° to 130° C.

COMPARATIVE EXAMPLE 1

The same procedures used in Example 1 were repeated except that 143 g of sodium 3,5-di-tert-butylsalicylate was substituted for 150 g of 3,5-di-tert-butyl-6-methylsalicylate to give 155 g of white powder. It was confirmed that the product corresponded to neutral zinc 3,5-di-tert-butylsalicylate . monohydrate on the basis of the results obtained according to analyses identical with those performed in Example 1 and that the product did not contain isopropanol molecules.

EXAMPLE 2

The same procedures used in Example 1 were repeated except that 200 g of 1,6-hexanediol was substituted for 300 g of isopropanol to give 190 g of white powder. The product was analyzed according to the same analyses as those performed in Example 1 and as a result it was found that the water content thereof was 2.56% (estimated theoretical value: 2.47%); the content of 1,6-hexanediol 15.9% (estimated theoretical value:

16.23%) and the zinc content 9.03% (estimated theoretical value: 8.98%). These results indicate that the product is, as estimated, a clathrate compound comprising, as the host crystal, neutral zinc 3,5-di-tert-butyl-6-methylsalicylate. monohydrate and one molecule of 1.6-hexanediol as the gest molecule. In addition, according to the NMR spectroscopic analysis of the product, it could not be distinguished from the mixture having the estimated ratio of the host crystal component to the gest molecular component.

EXAMPLE 3

The same procedures used in Example 1 were repeated except that 215 g of sodium 3,5-di-($\alpha,\alpha$-dimethylbenzyl)-6-methylsalicylate was substituted for 150 g of sodium 3,5-di-tert-butyl-6-methylsalicylate to give 255 g of white crystalline powder. The product was analyzed according to the same analyses as those performed in Example 1 and as a result it was found that the water content thereof was 1.92% (estimated theoretical value: 1.84%); the content of isopropanol 12.0% (estimated theoretical value: 12.28%) and the zinc content 6.71% (estimated theoretical value: 6.68%). These results indicate that the product is, as estimated, a clathrate compound comprising, as the host crystal, neutral zinc 3,5-di-($\alpha,\alpha$-dimethylbenzyl)-6-methylsalicylate . monohydrate and two molecules of isopropanol as the gest molecules. In addition, according to the NMR spectroscopic analysis of the clathrate compound, it could not be distinguished from the mixture having the estimated ratio of the host crystal component to the gest molecular component. When the product was subjected to thermal analysis, it was observed that a water molecule was released subsequently to the elimination of two isopropanol molecules at a temperature of 100° to 120° C.

COMPARATIVE EXAMPLE 2

The same procedures used in Example 1 were repeated except that 205 g of sodium 3,5-di-($\alpha,\alpha$-dimethylbenzyl) salicylate was substituted for 150 g of 3,5-ditert butyl-6-methylsalicylate to give 215 g of white powder. It was confirmed that the product corresponded to neutral zinc 3,5-di-($\alpha,\alpha$-dimethylbenzyl)salicylate . monohydrate on the basis of the results obtained according to analyses identical with those performed in Example 1 and that the product did not contain isopropanol molecules at all.

REFERENCE EXAMPLE 1

To a four-necked 2,000 ml volume flask of hard glass provided with a stirring machine, a thermometer, a dropping funnel and a reflux condenser, there were added 1,000 g of methanol and 40 g of water. The flask was heated with stirring to control the temperature of the contents of the flask to 40° C. 20 g of the clathrate compound prepared in Example 3 was charged to the flask. The clathrate compound was immediately dissolved in the contents of the flask to form a homogeneous solution, but the solution become turbid within about 30 minutes and crystals were separated out. 20 g each of the clathrate compound was repeatedly added to the flask at about 5-minute intervals so that the total amount of the compound was equal to 200 g. Immediately after the addition of the clathrate compound, the mixture was cooled to control the temperature of the contents to 20° C. The contents of the flask were filtered under suction and the resulting filter cake was dried at 50° C. and a humidity of 30% to give 170 g of white powder. The product was analyzed according to the same analyses as those performed in Example 1 and as a result it was found that the water content thereof was 2.21% (estimated theoretical value: 2.10%); and the zinc content 7.59% (estimated theoretical value: 7.62%). Thus, it was confirmed that the product was, as estimated, neutral zinc 3,5-di-( $\alpha,\alpha$-dimethylbenzyl)-6-methylsalicylate . monohydrate. A part of the product was taken, expanded on a petri dish as a thin layer, allowed to stand in a room maintained at about 20° C. and a humidity of about 80% overnight and then the water content thereof was determined. Thus, it was confirmed that the water content thereof was 6.15% (estimated theoretical value: 6.04%) and that the product was, as estimated, neutral zinc 3,5-di ($\alpha,\alpha$-dimethylbenzyl)-6-methylsalicylate . trihydrate. Moreover, the trihydrate reversibly released water molecules under conditions of a temperature of 50° C. and a humidity of 30% and melted at about 160° C. while releasing the last one molecule of water during the thermal analysis. Therefore, it could be recognized that one water molecule of the trihydrate was the water of crystallization for forming the host crystal and that the remaining two water molecules served as the gest molecules.

EXAMPLE 4

The same procedures used in Example 1 were repeated except that 200 g of 1,6-hexanediol was substituted for 300 g of isopropanol and that 215 g of sodium 3,5-di-($\alpha,\alpha$-dimethylbenzyl)-6-methylsalicylate was substituted for 150 g of sodium 3,5-di-tert-butyl-6-methylsalicylate to give 226 g of white crystalline powder. The product was analyzed according to the same analyses as those performed in Example 1 and as a result it was found that the water content thereof was 2.03% (estimated theoretical value: 1.84%); the content of 1,6-hexanediol 13.0% (estimated theoretical value: 12.10%) and the zinc content 6.72% (estimated theoretical value: 6.69%). Thus, it was confirmed that the product was, as estimated, a clathrate compound comprising, as the host crystal, neutral zinc 3,5-di-($\alpha,\alpha$-dimethylbenzyl)-6-methylsalicylate . monohydrate and one molecule of 1,6-hexanediol as the gest molecule.

In addition, according to the NMR spectroscopic analysis of the clathrate compound, it could not be distinguished from the mixture obtained by admixing neutral zinc 3,5-di-($\alpha,\alpha$-dimethylbenzyl)-6-methylsalicylate . monohydrate obtained in Reference Example 1 and 1,6-hexanediol so that the mixing ratio was equal to that of the product of this Example. When the product was subjected to thermal analysis, it was observed that the product melted at 202° C. and simultaneously water and 1,6-hexanediol were gradually released.

EXAMPLE 5

To a four-necked 2,000 ml volume flask of hard glass equipped with a stirring machine, a thermometer, a dropping funnel and a reflux condenser, there were added 1,400 g of water, 150 g of 1,6-hexanediol and 100 g of neutral zinc 3,5-di-($\alpha,\alpha$-dimethylbenzyl)-6-methylsalicylate . monohydrate obtained in Reference Example 1 and the flask was heated with stirring to thus maintain the temperature of the contents of the flask to 95° C. for 30 minutes. After gradually cooling the contents of the flask down to 25° C., they were then filtered under suction and the resulting filter cake was washed with 500 g of water. The product was dried at 60° C.

and 30 Torr to thus give 113 g of white crystalline powder. This product could not be analytically distinguished from the product of Example 4.

EXAMPLE 6

To a four-necked 1,000 ml volume flask of hard glass equipped with a stirring machine, a thermometer, a dropping funnel and a reflux condenser, there were added 100 g of benzene, 50 g of cyclohexanol and 100 g of the product of Reference Example 1. The contents of the flask was stirred to give a slightly viscous solution. When 200 ml of hexane was dropwise added to the contents through the droping funnel, the solution got cloudy within one hour to thus separate out crystals. Then additional 300 ml of hexane was dropwise added to the solution over 3 hours. After completion of the dropwise addition, the mixture was stirred for additional 3 hours and then the contents were filtered under suction. The resulting filter cake was washed with 500 ml of hexane and dried at 40° C. to give 107 g of white crystalline powder. The product was analyzed according to the same analyses as those performed in Example 1 and it was found that the product contained 1.98% of water (estimated theoretical value: 1.88%), 10.1% of cyclohexanol (estimated theoretical value: 10.45%) and 6.85% of zinc (estimated theoretical value: 6.82%). This fact indicates that the product is a clathrate compound comprising, as the host crystal, neutral zinc 3,5-di-($\alpha,\alpha$-dimethylbenzyl)-6-methylsalicylate . monohydrate and one molecule of cyclohexanol as the gest molecule. In addition, according to the NMR spectroscopic analysis of the clathrate compound, it could not be distinguished from the mixture of the product of Reference Example 1 and cyclohexanol having a mixing ratio equal to that of the product of this Example.

EXAMPLE 7

The same procedures used in Example 5 were repeated except that 19 g of 1,8-octanediol was substituted for 150 g of 1,6-hexanediol to give 113 g of white crystalline powder. The product was analyzed according to the same analyses as those performed in Example 1 and it was found that the product contained 1.92% of water (estimated theoretical value: 1.79%), 13.8% of 1,8-octanediol (estimated theoretical value: 14.50%) and 6.51% of zinc (estimated theoretical value: 6.48%). This fact indicates that the product is a clathrate compound comprising, as the host crystal, neutral zinc 3,5-di-($\alpha,\alpha$-dimethylbenzyl)-6-methylsalicylate . monohydrate and one molecule of 1,8-octanediol as the gest molecule.

EXAMPLE 8

The same procedures used in Example 5 were repeated except that 150 g of triethylene glycol was substituted for 150 g of 1,6-hexanediol to give 112 g of white crystalline powder. The product was analyzed according to the same analyses as those performed in Example 1 and it was found that the product contained 1.94% of water (estimated theoretical value: 1.79%), 14.9% of triethylene glycol (estimated theoretical value: 14.89%) and 6.6% of zinc (estimated theoretical value: 6.48%). This fact indicates that the product is a clathrate compound comprising, as the host crystal, neutral zinc 3,5-di-($\alpha,\alpha$-dimethylbenzyl)-6-methylsalicylate . monohydrate and one molecule of triethylene glycol as the gest molecule. When the product was subjected to thermal analysis, it was found that the clathrate compound had a clear melting point at 178° C., released the water molecules simultaneously with the melting and subsequently released the triethylene glycol molecules. The results of NMR spectroscopic analysis of the product were quite similar to those observed in the foregoing Examples.

EXAMPLE 9

The same procedures used in Example 5 were repeated except that 100 g of $\beta$-thiodiglycol was substituted for 150 g of 1,6-hexanediol to give 110 g of white crystalline powder. The product was analyzed according to the same analyses as those performed in Example 1 and it was found that the product contained 2.21% of water (estimated theoretical value: 1.84%), 12.5% of $\beta$-thiodiglycol (estimated theoretical value: 12.46%) and 6.80% of zinc (estimated theoretical value: 6.67%). This fact indicates that the product is a clathrate compound comprising, as the host crystal, neutral zinc 3,5-di-($\alpha,\alpha$-dimethylbenzyl)-6-methylsalicylate . monohydrate and one molecule of $\beta$-thiodiglycol as the gest molecule. The product was subjected to sulfur analysis and the sulfur content thereof was found to be 3.19% (estimated theoretical value: 3.27%). When the product was subjected to thermal analysis, it was observed that the compound was melted at 178° C., released the water molecules simultaneously with the melting and subsequently released the $\beta$-thiodiglycol molecules gradually. The results of NMR spectroscopic analysis of the product were quite similar to those observed in the foregoing Examples.

EXAMPLE 10

The same procedures used in Example 5 were repeated except that 100 g of diethylene glycol was substituted for 150 g of 1,6-hexanediol to give 109 g of white crystalline powder. The product was analyzed according to the same analyses as those performed in Example 1 and it was found that the product contained 2.18% of water (estimated theoretical value: 1.87%), 10.9% of diethylene glycol (estimated theoretical value: 11.00%) and 6.69% of zinc (estimated theoretical value: 6.78%). This fact indicates that the product is a clathrate compound comprising, as the host crystal, neutral zinc 3,5-di-($\alpha,\alpha$-dimethylbenzyl)-6-methylsalicylate . monohydrate and one molecule of diethylene glycol as the gest molecule. When the product was subjected to thermal analysis, it was observed that this compound was melted at 191° C., released the water molecules simultaneously with the melting and subsequently released the diethylene glycol molecules gradually. The results of NMR spectroscopic analysis of the product were identical with those observed in the foregoing Examples.

EXAMPLE 11

To a flask identical with that used in Example 6, there were added 150 g of benzene and 150 g of the product of Reference Example 1 and the mixture was stirred to dissolve the product in benzene. To the resulting solution, there was added 400 g of hexane and then 14 g of acetic acid was dropwise added to the mixture over about 5 hours with stirring. The solution in the flask got cloudy during the dropwise addition of acetic acid and crystals were separated out. After the dropwise addition, the solution was stirred for additional 2 hours and was filtered under suction. The resultant filter cake was washed with 300 g of hexane and dried to give 109 g of white crystalline powder. The product was analyzed according to the same analyses as those performed in Example 1 and it was found that the product contained 2.06% of water (estimated theoretical value: 1.84%), 13.1% of acetic acid (estimated theoretical value: 12.28%) and 6.75% of zinc (estimated theoretical value: 6.68%). This fact indicates that the product is a clathrate compound comprising, as the host crystal, neutral zinc 3,5-di-(α,α-dimethylbenzyl)-6-methylsalicylate . monohydrate and two molecules of acetic acid as the gest molecules.

EXAMPLE 12

To a flask similar to that used in Example 5, there were added 1,400 g of water, 150 g of β-thiodiglycol and 100 g of the product obtained in Example 1, the flask was heated with stirring to control the temperature of the contents of the flask to 95° C. and the contents was held at this temperature for 30 minutes. The contents of the flask was gradually cooled and was filtered under suction after the temperature thereof reached a temperature of not more than 30° C. The resulting filter cake was washed with 500 g of water and dried at 70° C. and a pressure of 30 Torr to thus give 100 g of white crystalline powder. The product was analyzed according to the same analyses as those performed in Example 1 and it was found that the product contained 0.31% of water (estimated theoretical value: 0%), 14.7% of thiodiglycol (estimated theoretical value: 15.23%) and 11.3% of zinc (estimated theoretical value: 11.04%). This fact indicates that the product is a clathrate compound comprising, as the host crystal, anhydrous zinc 3,5-di-tert-butyl-6-methylsalicylate and one molecule of β-thiodiglycol as the gest molecule. In addition, according to NMR spectroscopic analysis, the product differs from the mixture of the product of Example 1 and β-thiodiglycol having a mixing ratio identical with that of the product of this Example, in respect of the presence of one water molecule and two isopropanol molecules.

Industrial Applicability

The clathrate compound obtained in each Example is improved in particular in resistance to light rays and $NO_x$ gases. Developers for recording materials will be taken by way of example to explain specific test examples and to thus demonstrate the improvement in such properties while referring to the following Comparative Examples. An aqueous coating solution was prepared from a clathrate compound or a comparative compound and polyvinyl alcohol as an adhesive, the coating solution was applied onto the surface of paper so that the amount of the compound applied is about 10 g/m² and the paper was dried to give a developing sheet. The results of these test are summarized in the following Table.

The developability was determined by putting the resulting developing sheet on wood free paper for pressure-sensitive copying machines, printing with an electric typewriter, visually examining the developed density to evaluate the developability according to the following criteria:

| ⊚: very high; | ∘: high; |
|---|---|
| Δ: low; | x: very low. |

The weatherability was determined by directly exposing the resulting developing sheet to sunlight repeatedly for 3 fine weather days over 6 hours (from 9 o'clock in the morning to 3 o'clock in the afternoon) during the term of from Mar. 10 to Mar. 17 and examining the change in the whiteness of the developing sheet to evaluate the weatherability according to the following criteria:

| ⊚: no change; | ∘: slightly contaminated; |
|---|---|
| Δ: contaminated; | x: severely contaminated. |

In addition, the resistance to $NO_x$ gases was determined by examining the developing sheet according to the method of JIS L 0855 and evaluating the resistance according to the following criteria;

| ⊚: no change; | ∘: slightly contaminated; |
|---|---|
| Δ: contaminated; | x: severely contaminated. |

| Sample | Developability | Weatherability | Resistance to $NO_x$ |
|---|---|---|---|
| Example 1 | ⊚ | ∘ | ⊚ |
| Example 2 | ⊚ | ⊚ | ⊚ |
| Example 3 | ⊚ | ∘ | ⊚ |
| Example 4 | ⊚ | ⊚ | ⊚ |
| Example 5 | ⊚ | ⊚ | ⊚ |
| Example 6 | ⊚ | ∘ | ⊚ |
| Example 7 | ⊚ | ⊚ | ⊚ |
| Example 8 | ⊚ | ⊚ | ⊚ |
| Example 9 | ⊚ | ⊚ | ⊚ |
| Example 10 | ⊚ | ⊚ | ⊚ |
| Example 11 | ⊚ | ⊚ | ⊚ |
| Example 12 | ⊚ | ⊚ | ⊚ |
| Comparative Ex. A | ⊚ | Δ | ⊚ |
| Comparative Ex. B | ⊚ | Δ | Δ |
| Comparative Ex. C | x | ⊚ | ⊚ |
| Comparative Ex. D | Δ | ⊚ | ⊚ |

Comparative Ex. A: The product of Reference Example 1.
Comparative Ex. B: Zinc 3,5-di-tert-butyl-6-methylsalicylate.monohydrate
Comparative Ex. C: Zinc 3,5-di-(α,α-dimethylbenzyl) salicylate.monohydrate (the product of Comparative Example 2)
Comparative Ex. D: Zinc 3,5-di-tert-butylsalicylate.monohydrate (the product of Comparative Example 1)

I claim:
1. A clathrate compound of a nuclear-substituted salicylic acid salt which comprises, as a host, crystals of a zinc salt of a nuclear-substituted salicylic acid represented by the following general formula (I) or a hydrate thereof and, as a gest molecule, an organic compound having 1 to 12 carbon atoms:

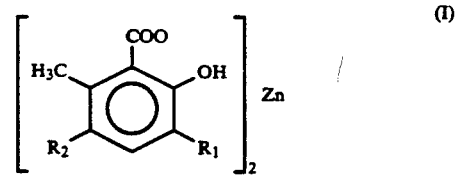

(I)

wherein $R_1$ and $R_2$ each represent a tert-butyl group, a tert-amyl group, a tert-octyl group or an α,α-dimethylbenzyl group.

2. The clathrate compound of claim 1 wherein the host crystal is zinc 3,5-di-tert-butyl-6-methylsalicylate or a hydrate thereof.

3. The clathrate compound of claim 1 wherein the host crystal is zinc 3,5-di-(α,α-dimethylbenzyl)-6-methylsalicylate or a hydrate thereof.

4. The clathrate compound of claim 1 wherein the gest molecule is an organic acid.

5. The clathrate compound of claim 1 wherein the gest molecule is an alcohol.

6. The clathrate compound of claim 1 wherein the gest molecule is a diol.

7. The clathrate compound of claim 1 wherein the gest molecule is a β-thiodiglycol.

* * * * *